United States Patent
Smith et al.

(10) Patent No.: US 6,387,620 B1
(45) Date of Patent: May 14, 2002

(54) TRANSCRIPTION-FREE SELEX

(75) Inventors: Jonathan Drew Smith; Larry Gold, both of Boulder, CO (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 09/362,578

(22) Filed: Jul. 28, 1999

(51) Int. Cl.[7] .................... C12Q 1/68; C12P 19/34; C07H 21/02; C07H 21/04; C07H 19/00
(52) U.S. Cl. .................... 435/6; 435/91.1; 435/91.2; 435/91.21; 435/91.3; 435/91.31; 435/91.4; 536/22.1; 536/24.31; 536/24.32; 536/24.33; 536/25.1; 536/25.32
(58) Field of Search .................... 435/6, 91.1, 91.2, 435/91.21, 91.3, 91.31, 91.32, 91.4, 91.41, 91.5, 91.51, 91.52; 536/24.3, 24.31, 24.33, 25.1, 24.5, 25.3, 25.32, 25.4, 25.41, 22.1

(56) References Cited

U.S. PATENT DOCUMENTS

| | | | | |
|---|---|---|---|---|
| 5,637,459 A | * | 6/1997 | Burke et al. .................... | 435/6 |
| 5,698,391 A | | 12/1997 | Cook et al. | |
| 5,707,796 A | * | 1/1998 | Gold et al. .................... | 435/6 |
| 5,723,323 A | | 3/1998 | Kauffman et al. | |

FOREIGN PATENT DOCUMENTS

| | | |
|---|---|---|
| GB | 2 183 661 A | 6/1987 |
| WO | WO89/06694 | 7/1989 |
| WO | WO 91/19813 | 12/1991 |
| WO | WO92/14843 | 9/1992 |

OTHER PUBLICATIONS

Joyce (1989) Gene 82:83.
Joyce & Inoue (1989) Nucleic Acids Research 17:711.
Ellington & Szostak (1990) Abstracts of papers presented at the 1990 meeting on RNA Processing, Cold Spring Harbor Laboratory, Cold Spring Harbor, NY, p. 84.
Kinzler & Vogelstein (1989) Nucleic Acids Research 17:3645.
Kramer et al. (1974) J. Mol. Biol. 89:719.
Levisohn & Spieglman (1969) Proc. Natl. Acad. Sci. USA 63:805.
Levisohn & Spiegelman (1968) Proc. Natl. Acad. Sci. USA 60:866.
Oliphant et al. (1989) Mol. Cell. Biol. 9:2944.
Oliphant & Struhl (1988) Nucleic Acids Research 16:7673.
Oliphant & Struhl (1987) Methods in Enzymology 155:568.
Oliphant et al. (1986) Gene 44:177.
Robertson & Joyce (1990) Nature 344:467.
Thiesen & Bach (1990) Nucleic Acids Research 18:3203.
Szostak, "Structure and Activity of Ribozymes," in *Redesigning the Molecules of Life*, (S.A. Benner ed.) Springer–Verlag Berline Heidelberg, pp. 87–113 (1988).

* cited by examiner

*Primary Examiner*—Jeffrey Siew

(57) ABSTRACT

Methods are provided for the production of nucleic acid ligands against target molecules using a procedure known as Transcription-free Systematic Evolution of Ligands by EXponential enrichment (Transcription-free SELEX). The Transcription-free SELEX method assembles nucleic acid ligands from fragments of synthetic nucleic acids by annealing those fragments to a complementary template, and then ligating the fragments together.

9 Claims, 3 Drawing Sheets

TRANSCRIPTION-FREE SELEX

FIELD OF THE INVENTION

This invention is directed to a method for the generation of nucleic acid ligands having specific functions against target molecules using the SELEX process. The invention provides a method of producing candidate mixtures of RNA nucleic acid ligands without using transcription. The instant methods allow SELEX to be performed using modified ribonucleotides that cannot serve as efficient substrates for RNA polymerases.

BACKGROUND OF THE INVENTION

The dogma for many years was that nucleic acids had primarily an informational role. Through a method known as Systematic Evolution of Ligands by EXponential enrichment, termed the SELEX process, it has become clear that nucleic acids have three dimensional structural diversity not unlike proteins. The SELEX process is a method for the in vitro evolution of nucleic acid molecules with highly specific binding to target molecules and is described in U.S. patent application Ser. No. 07/536,428, filed Jun. 11, 1990, entitled "Systematic Evolution of Ligands by EXponential Enrichment," now abandoned, U.S. Pat. No. 5,475,096 entitled "Nucleic Acid Ligands", U.S. Pat. No. 5,270,163 (see also WO 91/19813) entitled "Nucleic Acid Ligands" each of which is specifically incorporated by reference herein. Each of these applications, collectively referred to herein as the SELEX Patent Applications, describes a fundamentally novel method for making a nucleic acid ligand to any desired target molecule. The SELEX process provides a class of products which are referred to as nucleic acid ligands or aptamers, each having a unique sequence, and which has the property of binding specifically to a desired target compound or molecule. Each SELEX-identified nucleic acid ligand is a specific ligand of a given target compound or molecule. The SELEX process is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets in the SELEX method. The SELEX method applied to the application of high affinity binding involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule.

It has been recognized by the present inventors that the SELEX method demonstrates that nucleic acids as chemical compounds can form a wide array of shapes, sizes and configurations, and are capable of a far broader repertoire of binding and other functions than those displayed by nucleic acids in biological systems.

The basic SELEX method has been modified to achieve a number of specific objectives. For example, U.S. patent application Ser. No. 07/960,093, filed Oct. 14, 1992, now abandoned, and U.S. Pat. No. 5,707,796, both entitled "Method for Selecting Nucleic Acids on the Basis of Structure," describe the use of the SELEX process in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands,", now abandoned, U.S. Pat. No. 5,763,177 entitled "Systematic Evolution of Nucleic Acid Ligands by Exponential Enrichment: Photoselection of Nucleic Acid Ligands and Solution SELEX" and U.S. patent application Ser. No. 09/093,293, filed Jun. 8 1998, entitled "Systematic Evolution of Nucleic Acid Ligands by Exponential Enrichment: Photoselection of Nucleic Acid Ligands and Solution SELEX," now U.S. Pat. No. 6,001,577, describe a SELEX based method for selecting nucleic acid ligands containing photoreactive groups capable of binding and/or photocrosslinking to and/or photoinactivating a target molecule. U.S. Pat. No. 5,580,737 entitled "High-Affinity Nucleic Acid Ligands That Discriminate Between Theophylline and Caffeine," describes a method for identifying highly specific nucleic acid ligands able to discriminate between closely related molecules, which can be non-peptidic, termed Counter-SELEX. U.S. Pat. No. 5,567,588 entitled "Systematic Evolution of Ligands by EXponential Enrichment: Solution SELEX," describes a SELEX-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX process-identified nucleic acid ligands containing modified nucleotides are described in U.S. Pat. No. 5,660,985 entitled "High Affinity Nucleic Acid Ligands Containing Modified Nucleotides," that describes oligonucleotides containing nucleotide derivatives chemically modified at the 5- and 2'-positions of pyrimidines. U.S. Pat. No. 5,580,737, supra, describes highly specific nucleic acid ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of 2' Modified Pyrimidine Intramolecular Nucleophilic Displacement," describes oligonucleotides containing various 2'-modified pyrimidines.

The SELEX method encompasses combining selected oligonucleotides with other selected oligonucleotides and non-oligonucleotide functional units as described in U.S. Pat. No. 5,637,459 entitled "Systematic Evolution of Ligands by EXponential Enrichment: Chimeric SELEX," and U.S. Pat. No. 5,683,867 entitled "Systematic Evolution of Ligands by EXponential Enrichment: Blended SELEX," respectively. These applications allow the combination of the broad array of shapes and other properties, and the efficient amplification and replication properties, of oligonucleotides with the desirable properties of other molecules.

The SELEX method further encompasses combining selected nucleic acid ligands with lipophilic compounds or non-immunogenic, high molecular weight compounds in a diagnostic or therapeutic complex as described in U.S. patent application Ser. No. 08/434,465, filed May 4, 1995, now U.S. Pat. No. 6,011,020 Jan. 4, 2000 entitled "Nucleic Acid Complexes". Each of the above described patent applications which describe modifications of the basic SELEX procedure are specifically incorporated by reference herein in their entirety.

The central method for identifying nucleic acid ligands to a target is called the SELEX process, an acronym for Systematic Evolution of Ligands by Exponential enrichment and involves (a) contacting the candidate mixture of nucleic acids the target, (b) partitioning between members of said candidate mixture on the basis of affinity to the target, and (c) amplifying the selected molecules to yield a mixture of nucleic acids enriched for nucleic acid sequences with a relatively higher affinity for binding to the target.

In typical embodiments of the SELEX process, the candidate mixture of nucleic acid ligands comprises RNA molecules. Following partitioning step (b) above, the RNA molecules that have higher affinity for the target are reverse transcribed to form a DNA template. This DNA template is then amplified by the Polymerase Chain Reaction (PCR), and the amplified DNA molecules are transcribed in order to provide a new RNA candidate mixture for the next round of the SELEX process.

Although the transcription of DNA templates during the SELEX process to form RNA nucleic acid ligand candidate mixtures is generally efficient, problems can arise when attempting to incorporate modified ribonucleotides into the RNA molecules during transcription. Such modified ribonucleotides increase the functionality and stability of candidate nucleic acid ligands, but are often poor substrates for RNA polymerase. As a result, transcription in the presence of such modified ribonucleotides is often inefficient, leading to poor yields, or does not take place at all. For example, it is often desirable to incorporate 2'-O alkyl ribonucleotides (ribonucleotides that have an alkyl grouping at the 2' oxygen), such as 2'-OMe (a methyl group at the 2' oxygen), into the candidate RNA nucleic acid ligands because such ribonucleotides confer great stability to the RNA. However, no transcription takes place in the presence of 2'-OMe ribonucleotides because these modified ribonucleotides are not substrates for RNA polymerase.

Typical SELEX procedures permit the incorporation, at most, of 5 different modified nucleotides into a candidate mixture (one for each of the 4 NTPs incorporated during the elongation phase of transcription, and one nucleoside, NMP or NDP incorporated at the 5' end at initiation of transcription). With the exception of the 5' modification, these modifications are distributed randomly, with respect to both number and position, throughout the randomized portion of the transcript. This random distribution can be a disadvantage, particularly when chemically reactive modifications, or modifications which reduce the solubility or stability of the transcript are introduced.

It is an object of the present invention to provide a method for performing the SELEX process in which modified ribonucleotides, such as 2'-OMe ribonucleotides, are efficiently incorporated into RNA candidate mixtures. It is a further object of the invention to provide a method for performing the SELEX process in which modified ribonucleotides can be incorporated at specific positions.

SUMMARY OF THE INVENTION

The instant invention provides novel methods for performing the SELEX process to obtain nucleic acid ligands to target compounds. In particular, methods are provided for obtaining candidate mixtures of nucleic acid ligands comprised of RNA without requiring transcription. Instead of transcription, the candidate RNA nucleic acid ligands are prepared by annealing at least partially randomized RNA fragments to at least partially randomized DNA templates. The annealed RNA fragments are then ligated together to form the candidate nucleic acid ligands. The RNA fragments can be fully synthetic, and so can be comprised of modified ribonucleotide subunits that cannot be incorporated into RNA by RNA polymerase during transcription. Thus, the instant invention allows the SELEX process to be performed with more diverse nucleic acid chemistries than was previously possible.

DETAILED DESCRIPTION OF THE INVENTION

Definitions

Figure 1:
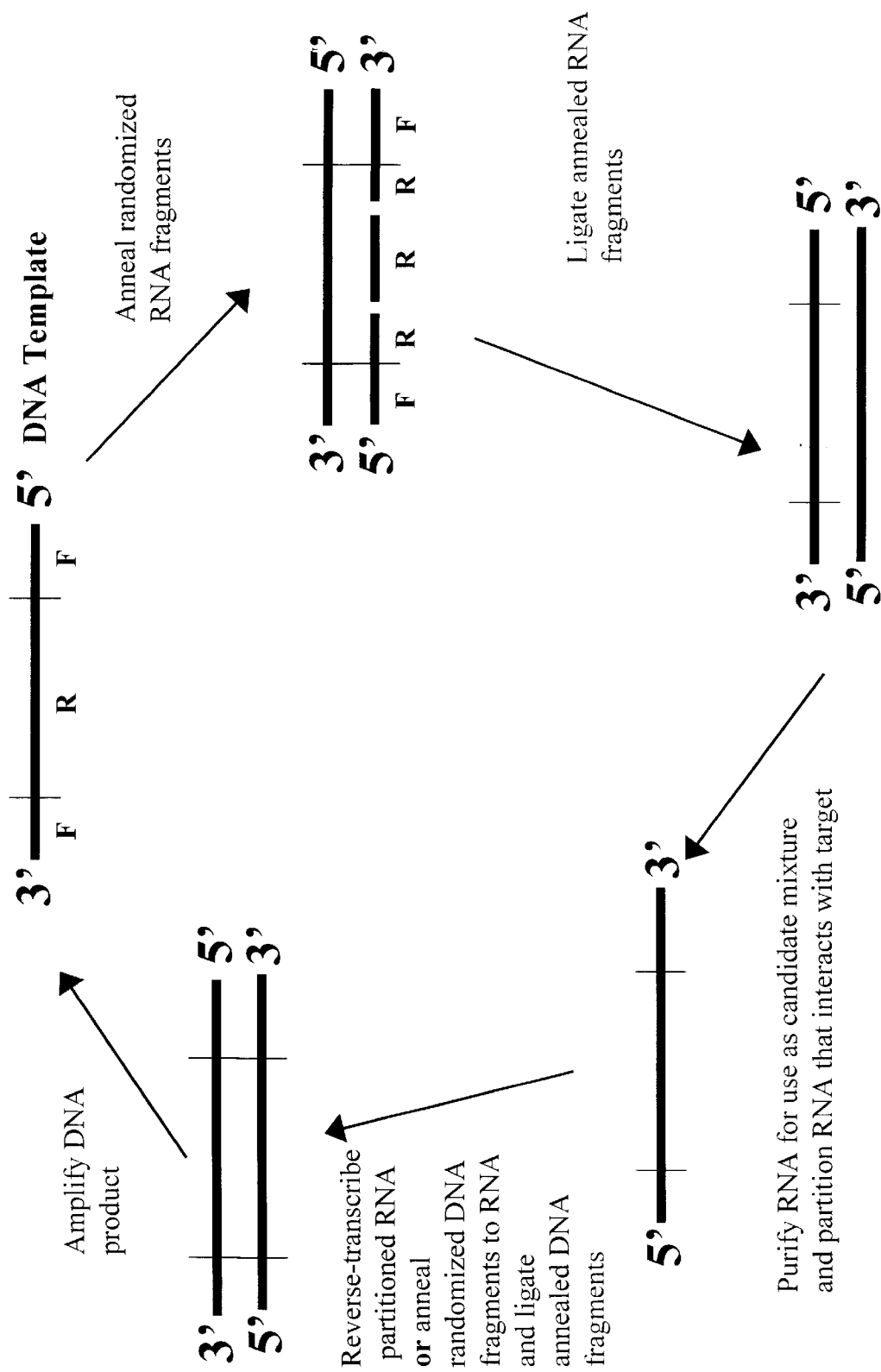
FIG. 1 shows a schematic representation of one embodiment of the Transcription-free SELEX process. A DNA template library comprising randomized (R) and fixed (F) sequence regions is contacted with a 3 libraries of RNA fragments comprising randomized regions and fixed regions complementary to the fixed regions of the DNA template. After annealing in the correct register, the RNA fragments are ligated together, and the RNA is partitioned from the DNA template to provide a candidate mixture of nucleic acid ligands. The candidate mixture of nucleic acid ligands is contacted with a target molecule of interest; nucleic acid ligands that interact with the target in the desired manner are partitioned from those that do not. The nucleic acid ligands that interact with the target in the desired manner are then reverse transcribed to yield complementary DNA templates. Alternatively, if the nucleic acid ligands are comprised of ribonucleotides that are not compatible with reverse transcriptase, then the DNA templates are assembled by annealing DNA fragments to the nucleic acid ligands, and then ligating those DNA fragments together. In either case, these DNA templates can then serve as templates for RNA fragment annealing in a further optional cycle of the Transcription-free SELEX method.

Various terms are used herein to refer to aspects of the present invention. To aid in the clarification of the description of the components of this invention, the following definitions are provided:

As used herein, "nucleic acid ligand" is a non-naturally occurring nucleic acid having a desirable action on a target. Nucleic acid ligands are often referred to as "aptamers". A desirable action includes, but is not limited to, binding of the target, catalytically changing the target, reacting with the target in a way which modifies/alters the target or the functional activity of the target, covalently attaching to the target as in a suicide inhibitor, facilitating the reaction between the target and another molecule. In the preferred embodiment, the action is specific binding affinity for a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule. Nucleic acid ligands include nucleic acids that are identified from a candidate mixture of nucleic acids, said nucleic acid ligand being a ligand of a given target, by the method comprising: a) contacting the candidate mixture with the target, wherein nucleic acids having an increased affinity to the target relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids.

As used herein, "candidate mixture" is a mixture of nucleic acids of differing sequence from which to select a desired ligand. The source of a candidate mixture can be from naturally-occurring nucleic acids or fragments thereof, chemically synthesized nucleic acids, enzymatically synthesized nucleic acids or nucleic acids made by a combination of the foregoing techniques. In a preferred embodiment, each nucleic acid has fixed sequences surrounding a randomized region to facilitate the amplification process. In preferred embodiments of the instant invention, the candidate mixture is comprised of synthetic RNA molecules that are assembled from smaller RNA fragments.

"SELEX target" or "target" means any compound or molecule of interest for which a ligand is desired. A target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation.

As used herein, "nucleic acid" means either DNA, RNA, single-stranded or double-stranded, and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping. In the instant invention, one preferred modification is the positioning of a methyl group at the 2'- oxygen of ribonucleotides.

"SELEX" methodology involves the combination of selection of nucleic acid ligands which interact with a target in a desirable manner, for example binding to a protein, with amplification of those selected nucleic acids. Optional iterative cycling of the selection/amplification steps allows selection of one or a small number of nucleic acids which interact most strongly with the target from a pool which contains a very large number of nucleic acids. Cycling of the selection/ amplification procedure is continued until a selected goal is achieved. The SELEX process is described in U.S. patent application Ser. No. 07/536,428, entitled Systematic Evolution of Ligands by Exponential Enrichment, now abandoned, U.S. Pat. No. 5,475,096 entitled nucleic acid ligands, U.S. Pat. No. 5,270,163 (see also WO 91/19813) entitled nucleic acid ligands. These patents and applications, each specifically incorporated herein by reference, are collectively called the SELEX Patent Applications.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity for the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The basic SELEX method has been modified to achieve a number of specific objectives. For example, U.S. patent application Ser. No. 07/960,093, filed Oct. 14, 1992, now abandoned, and U.S. Pat. No. 5,707,796 both entitled "Method for Selecting Nucleic Acids on the Basis of Structure," describe the use of the SELEX process in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands," now abandoned, U.S. Pat. No. 5,763,177 entitled "Systematic Evolution of Nucleic Acid Ligands by Exponential Enrichment: Photoselection of Nucleic Acid Ligands and Solution SELEX" and U.S. patent application Ser. No. 09/093,293, filed Jun. 8 1998, now U.S. Pat. No. 6,001,577 Dec. 14, 2000 entitled "Systematic Evolution of Nucleic Acid Ligands by Exponential Enrichment: Photoselection of Nucleic Acid Ligands and Solution SELEX" all describe a SELEX based method for selecting nucleic acid ligands containing photoreactive groups capable of binding and/or photocrosslinking to and/or photoinactivating a target molecule. U.S. Pat. No. 5,580,737 entitled "High-Affinity Nucleic Acid Ligands That Discriminate Between Theophylline and Caffeine," describes a method for identifying highly specific nucleic acid ligands able to discriminate between closely related molecules, termed Counter-SELEX. U.S. Pat. No. 5,567,588 entitled "Systematic Evolution of Ligands by Exponential Enrichment: Solution SELEX," describes a SELEX-based method which achieves highly efficient partitioning between oligonucleotides having high and low affinity for a target molecule. U.S. Pat. No. 5,496,938 entitled "Nucleic Acid Ligands to HIV-RT and HIV-1 Rev," describes methods for obtaining improved nucleic acid ligands after SELEX has been performed. U.S. Pat. No. 5,705,337 entitled "Systematic Evolution of Ligands by Exponential Enrichment: Chemi-SELEX," describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. Pat. No. 5,660,985 entitled "High Affinity Nucleic Acid Ligands Containing Modified Nucleotides," that describes oligonucleotides containing nucleotide derivatives chemically modified at the 5- and 2'-positions of pyrimidines. U.S. Pat. No. 5,637,459, supra, describes highly specific nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, now abandoned entitled "Novel Method of Preparation of Known and Novel 2' Modified Nucleosides by Intramolecular Nucleophilic Displacement," describes oligonucleotides containing various 2'-modified pyrimidines.

The SELEX method encompasses combining selected oligonucleotides with other selected oligonucleotides and non-oligonucleotide functional units as described in U.S. Pat. No. 5,637,459 entitled "Systematic Evolution of Ligands by Exponential Enrichment: Chimeric SELEX," and U.S. Pat. No. 5,683,867 entitled "Systematic Evolution of Ligands by Exponential Enrichment: Blended SELEX," respectively. These applications allow the combination of the broad array of shapes and other properties, and the efficient amplification and replication properties, of oligonucleotides with the desirable properties of other molecules.

In U.S. Pat. No. 5,496,938, methods are described for obtaining improved nucleic acid ligands after the SELEX process has been performed. This patent, entitled "Methods of Producing nucleic acid ligands," is specifically incorporated herein by reference.

The SELEX process provides a class of products which are nucleic acid molecules, each having a unique sequence, and each of which has the property of binding specifically to a desired target compound or molecule. Target molecules are preferably proteins, but can also include among others carbohydrates, peptidoglycans and a variety of small molecules. SELEX methodology can also be used to target biological structures, such as cell surfaces or viruses, through specific interaction with a molecule that is an integral part of that biological structure.

One potential problem encountered in the diagnostic use of nucleic acids is that oligonucleotides in their phosphodiester form may be quickly degraded in body fluids by intracellular and extracellular enzymes such as endonucleases and exonucleases before the desired effect is manifest. Certain chemical modifications of the nucleic acid ligand can be made to increase the in vivo stability of the nucleic acid ligand or to enhance or to mediate the delivery of the nucleic acid ligand. See, e.g., U.S. patent application Ser. No. 08/117,991, filed Sep. 9, 1993, now abandoned, and U.S. Pat. No. 5,660,985, both entitled "High Affinity Nucleic Acid Ligands Containing Modified Nucleotides", which is specifically incorporated herein by reference. Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, methyl phosphonates, H-phosphonates, peptide modifications, unusual base-pairing combinations such as the isobases isocytidine and isoguanidine and the like. Modifications can also include 3' and 5' modifications such as capping, 3' or 5' sulfurs, and 3' or 5' amines. Any nucleic acid chemistry in which the modified nucleic acid is still able to form a double-helix with a complementary sequence is contemplated in the instant invention.

The modifications can be pre- or post-SELEX process modifications. Pre-SELEX process modifications yield nucleic acid ligands with both specificity for their SELEX target and improved in vivo stability. Post-SELEX process modifications made to 2'-OH nucleic acid ligands can result in improved in vivo stability without adversely affecting the binding capacity of the nucleic acid ligand. The instant invention provides methods for performing SELEX using modified nucleic acids in the candidate mixture.

Other modifications are known to one of ordinary skill in the art. Such modifications may be made post-SELEX process (modification of previously identified unmodified ligands) or by incorporation into the SELEX process.

In some embodiments, the nucleic acid ligands become covalently attached to their targets upon irradiation of the nucleic acid ligand with light having a selected wavelength. Methods for obtaining such nucleic acid ligands are detailed in U.S. patent application Ser. No. 08/123,935, filed Sep. 17, 1993, entitled "Photoselection of Nucleic Acid Ligands,", now abandoned, U.S. Pat. No. 5,763,177 entitled "Systematic Evolution of Nucleic Acid Ligands by Exponential Enrichment: Photoselection of Nucleic Acid Ligands and Solution SELEX" and U.S. Patent Application Serial No. 09/093,293, filed Jun. 8 1998, now U.S. Pat. No. 056,001, 577 Dec. 14, 1999 entitled "Systematic Evolution of Nucleic Acid Ligands by Exponential Enrichment: Photoselection of Nucleic Acid Ligands and Solution SELEX" each of which is specifically incorporated herein by reference in its entirety.

As used herein "synthetic RNA" means a ribonucleotide polymer that is assembled in vitro without the use of an enzyme. Any chemical system known in the art for ribonucleotide polymer synthesis is contemplated, including both solid-phase and solution-phase chemistries.

As used herein "library" means a population of nucleic acid molecules of constant length in which the individual members of the population differ in sequence from one another at predetermined positions. An individual library can have one or more fixed sequence regions—where every member of the library has the same bases at particular positions—and randomized regions. The randomized regions can be partly or completely randomized. Preferred embodiments of the instant invention uses three libraries: a first library in which the individual nucleic acid molecules have a 5' randomized region adjacent to a 3' fixed region; a second library in which the individual nucleic acid molecules have a 5' fixed region adjacent to a 3' randomized region; and a third library in which the individual nucleic acid molecules are randomized throughout their length.

As used herein "fragment" means an individual nucleic acid molecule obtained from a library. A fragment is typically shorter than an individual nucleic acid ligand.

Transcription-free SELEX

In some embodiments of the SELEX process, the candidate mixture of nucleic acid ligands comprises RNA molecules. In such embodiments, the SELEX process may comprise the following steps:

(a) providing a DNA template library comprising fixed 3' and 5' sequences, and random internal sequences;

(b) transcribing said DNA library from one of said fixed sequences to form a candidate mixture of RNA nucleic acid ligands;

(c) purifying said candidate mixture of RNA nucleic acid ligands from the DNA template library, and contacting said candidate mixture of RNA nucleic acid ligands with a target;

(d) partitioning RNA nucleic acid ligands that interact with the target in the desired manner from those that do not;

(e) reverse transcribing those RNA nucleic acid ligands that interact with the target in the desired manner to form DNA templates;

(f) amplifying said DNA templates using the Polymerase Chain Reaction with primers that hybridize to said fixed 5' and 3' sequences; and optionally;

(g) repeating steps (b)–(f) for the desired number of cycles.

The present invention accomplishes the SELEX process outlined above without requiring that transcription occurs at step (b) and, optionally, without requiring that reverse transcription occurs at step (e). Instead, the instant invention uses one or more randomized libraries of synthetic RNA molecules to directly assemble complementary RNA molecules on the DNA template of step (b). When contacted with the DNA template of step (b), the randomized synthetic RNA molecules anneal to the template. The individual RNA fragments can be ligated together, and the resulting RNA molecules can then be purified for use as the candidate mixture of nucleic acid ligands as described above. In turn, the candidate mixture of nucleic acid ligands can serve as templates for assembly of DNA using DNA fragments that anneal to the RNA molecules and are then ligated together. The resulting DNA can be PCR amplified, and then serve as the DNA template for the next round of the SELEX method. In this way, it is possible to produce candidate mixtures of RNA nucleic acid ligands from DNA templates without requiring transcription, and then optionally to produce DNA templates from RNA nucleic acid ligands without requiring reverse transcription. The method is termed Transcription-free SELEX.

In one embodiment of the Transcription-free SELEX method, the following steps take place (FIG. 1):

(a) providing a DNA library comprising fixed 3' and 5' sequences, and random internal sequences;

(b) contacting said DNA library with one or more synthetic libraries comprising randomized RNA fragments, wherein said fragments anneal to said DNA library to form substantially contiguous RNA molecules complementary to individual members of said DNA library;

(c) ligating said RNA fragments together to form a candidate mixture of RNA nucleic acid ligands;

(d) purifying said candidate mixture of RNA nucleic acid ligands from said DNA library, and contacting said candidate mixture of RNA nucleic acid ligands with a target;

(e) partitioning RNA nucleic acid ligands that interact with the target in the desired manner from those that do not;

(f) reverse transcribing those RNA nucleic acid ligands that interact with the target in the desired manner to form DNA templates;

(g) amplifying those DNA templates using the Polymerase Chain Reaction with primers that hybridize to said fixed 5' and 3' sequences; and optionally (h) repeating steps (b)–(g) for the desired number of cycles.

The primary advantage of using synthetic RNA fragments to assemble candidate mixtures of RNA nucleic acid ligands, rather than transcription, is that modified ribonucleotides can be more readily incorporated into the nucleic acid ligands. Such modified ribonucleotides are often poor substrates for RNA polymerase, and so yields of transcription are poor or non-existent. For example, in some embodiments it is desirable to use RNA nucleic acid ligands that are 2'-OMe. 2'-OMe ribonucleotides confer stability from ribonucleases upon RNA nucleic acid ligands. However, RNA polymerase does not incorporate 2'-OMe ribonucleotides into RNA, so no RNA is produced. In the Transcription-free SELEX method, by contrast, the RNA fragments can be chemically synthesized with 2'-OMe ribonucleotides by any technique known in the art. By ligating 2'-OMe RNA fragments together, a 2'-OMe candidate mixture of RNA nucleic acid ligands is efficiently produced without transcription. The Transcription-free SELEX method will allow functional activities to be included at defined sites, including but not limited to nucleophiles, RGD peptides, cages, and PEG groups (see below).

Preferred embodiments of the invention use libraries of randomized and partly randomized synthetic RNA fragments. The partly randomized RNA fragments comprise random sequence regions and fixed sequence regions, wherein the fixed sequence regions are complementary in sequence to the fixed sequence regions of the DNA template. Thus, partly randomized fragments anneal to the fixed regions of the DNA template and to the adjacent random sequence region of the DNA template. The fixed sequence regions anneal rapidly (due to their higher concentration relative to each random sequence) and thus set the "register" for annealing the filly randomized RNA molecules. This favors products of the correct size, and is necessary for position specific modification (see below). The individual randomized and partly randomized RNA molecules that have annealed along the length of the DNA template can then be ligated together to form a continuous RNA strand, complementary in sequence to the DNA template.

Figure 2:
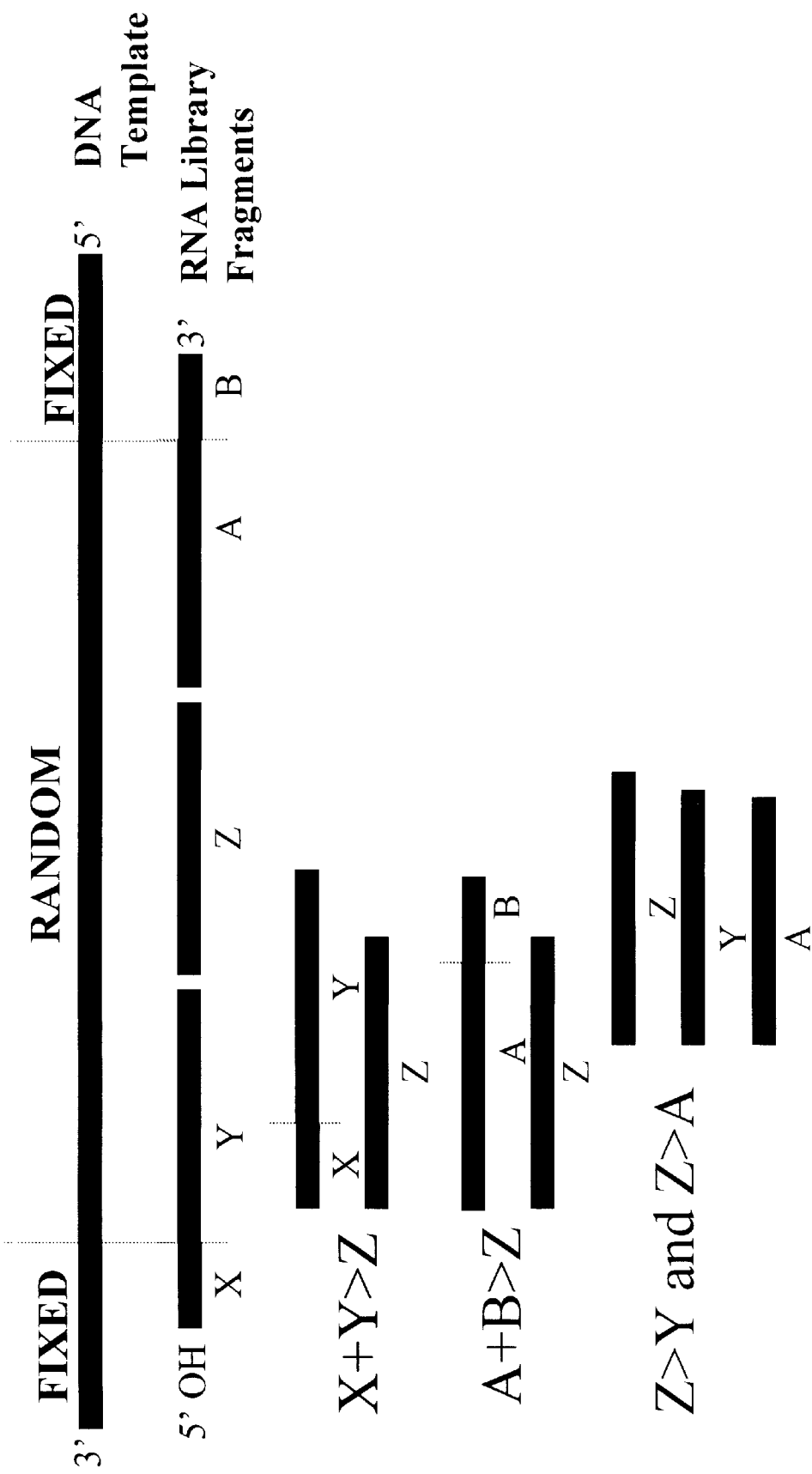
FIG. 2 shows a schematic representation of 3 random and partly random RNA libraries annealed to a typical SELEX DNA template. The relative sizes of the fixed and random sequence regions of the RNA libraries insures that at equilibrium, the most stable configuration of the individual library fragments is the one illustrated.

In preferred embodiments of the invention, at least 3 separate RNA libraries are used. A schematic representation of these libraries is given in FIG. 2. A first library has a randomized sequence 3' region X nucleotides long and a fixed sequence 5' region Y nucleotides long that is complementary to the 3' fixed sequence region of the DNA template; the second library has a randomized sequence 5' region A nucleotides long and a fixed sequence 3' region B nucleotides long that is complementary to the fixed 5' region of the DNA template; the third library is Z nucleotides of random sequence. The total length of the randomized portions of the three libraries is equal to the length of the randomized portion of the DNA template (X+A+Z=DNA template random region). The total length of each RNA molecule in the first and second library is greater than that of each molecule in the third library (X+Y>Z; A+B>Z); the randomized portions of the first and second libraries are preferably shorter than the totally randomized molecules of the third population (X<Z; A<Z). These sequences anneal to DNA templates as shown in FIG. 2.

By using a plurality of randomized RNA fragments, rather than using randomized RNA molecules of the same size as the DNA template, the time taken for hybridization along the entire length of the DNA template is dramatically reduced. For example, the time taken to allow a random library of 30 mer RNA molecules to anneal to a 30 mer DNA template is approximately $10^4$ years, whereas using three random libraries of shorter RNA fragments takes only 1–2 hours to go to completion. Furthermore, by endowing the first and second populations with regions complementary to the fixed sequences in the DNA template, these RNA fragments are kept in proper register. Because the randomized portions of the first and second libraries are shorter than in the third library (X<Z; A<Z), the annealing of the third library to the DNA template will displace any first and second library RNA fragments that have annealed to the randomized region of the DNA template without annealing to the fixed regions also. Similarly, because the first and second library RNA fragments are longer than the third population RNA fragments, correctly annealed first and second library RNA fragments will not be displaced by third library molecules that fortuitously hybridize to the same sequence. Thus, the relative lengths of the random and fixed sequence regions of the three libraries insures that the thermodynamically most stable configuration occurs when the three RNA fragments anneal to the DNA template as shown in FIG. 2.

Although the embodiment described above uses 3 populations, any number of RNA fragments can be used. Indeed, in some applications it may be desirable to use a greater number. For example, it is known that in some SELEX reactions, a single dominant sequence may comprise ~10% of the library. If the third population RNA fragments (fully randomized) are, for example, 11 nucleotides long, and if there is a 5-fold excess of these RNA fragments over DNA template, then only $\frac{1}{4}^{11}=1/(4 \times 10^6)$ of the RNA fragments will possess the correct sequence to anneal to the dominant sequence. This may mean that the dominant sequence will be poorly amplified in later SELEX rounds. Using RNA fragments shorter than 11 nucleotides that are present at a much larger excess than 5-fold will allow more efficient amplification of the dominant sequence.

It will be appreciated from the foregoing that there are a number of variables that may be readily adjusted in order to obtain maximum efficiency in a particular Transcription-free SELEX application. The ability to manipulate such variables gives the Transcription-free SELEX method a high degree of flexibility. Manipulable variables include without limitation: the number of populations of randomized and partly randomized RNA fragments; the length of the individual RNA molecules in each population; the concentrations of the RNA molecules in each population; the length of the fixed sequence regions in partly randomized RNA fragment populations; and the time and temperature at which the hybridization occurs. The determination of these variables requires only routine experimentation for those skilled in the art.

The Transcription-free SELEX method provides a means to control the number and position of the modified nucleotides introduced into a candidate mixture of nucleic acid ligands. Consider a candidate mixture of RNA nucleic acid ligands assembled according to the example shown in FIG. 2. Each of the library RNA fragments is the product of a separate synthesis, and each occupies a unique site on the DNA template. It is possible to specify, for instance, that all of the uridines in the RNA fragment that anneals to the 5' end of the DNA template are modified in one way (e.g., 2'OMe), all of the uridines in the central RNA fragment are modified in a second way (e.g., BrdU), and all of the uridines in the RNA fragment that anneals to the 3' end of the DNA template are modified in a third way (e.g., 5-aminobenzoyl). This method can be used for all four nucleotides in each library of RNA fragments.

This concept can be extended to the level of the individual nucleotide, limited in practice only by the number of ports available on the synthesizer. That is, one could specify that uridines at position 1 of an RNA fragment are modification 1, uridines at position 2 are modification 2 etc. The number of different modifications incorporated into the library is thus limited only by the ability to synthesize the oligo libraries. The present invention contemplates the use of any nucleic acid chemistry in which the modified nucleic acid is able to form a double helix with a complementary nucleic acid sequence.

In preferred embodiments of the invention, the individual RNA fragments are ligated together following annealing by adding T4 DNA ligase to the reaction mixture. It is preferable to add ligase at the end of the annealing process, otherwise kinetic intermediates (incompletely and inappropriately annealed RNA fragments) will be ligated together.

Some of the modified ribonucleotides contemplated may serve as poor substrates for ligase; RNA fragments containing such modified ribonucleotides may therefore be ligated together with low efficiency. In such cases, the synthetic RNA molecules can be designed such that the particular ribonucleotide modification is not present at the critical positions of the RNA fragment needed for efficient RNA ligase function. In other embodiments, ligation may be achieved chemically without the use of ligase. A variety of chemical ligation procedures have been described in the scientific literature, including: carbodiimide condensation, as described in Dolinnaya, N. G., N. I. Sokolova, et al. (1988). "Site-directed modification of DNA duplexes by chemical ligation." Nucleic Acids Res. 16(9): 3721–38; cyanogen bromide condensation as described in Dolinnaya, N. G., N. I. Sokolova, et al. (1991). "The use of BrCN for assembling modified DNA duplexes and DNA-RNA hybrids; comparison with water-soluble carbodiimide." Nucleic Acids Res. 19(11): 3067–72; and sulfur-halide nucleophilic displacement as described in Xu, Y. and E. T. Kool (1999). "High sequence fidelity in a non-enzymatic DNA autoligation reaction." Nucleic Acids Res. 27(3): 875–81. Each of the foregoing references is incorporated herein by reference in its entirety. The fidelity of the reactions, and the activity of the resultant products has also been demonstrated as described in Housby, J. N. and E. M. Southern (1998). "Fidelity of DNA ligation: a novel experimental approach based on the polymerisation of libraries of oligonucleotides." NAR 26: 4259–4266; James, K. D., A. R. Boles, et al. (1998). "The fidelity of template-directed oligonucleotide ligation and its relevance to DNA computation." Nucleic Acids Research 26(22): 5203–5211; James, K. D. and A. D. Ellington (1997). "Surprising fidelity of template-directed chemical ligation of oligonucleotides." Chem. Biol. 4(8): 595–605; and Shabarova, Z. A., I. N. Merenkova, et al. (1991). "Chemical ligation of DNA: the first non-enzymatic assembly of a biologically active gene." Nucleic Acids Res. 19(15): 4247–51, each of which is incorporated herein by reference in its entirety.

In the embodiments described above, the synthetic RNA candidate mixture that is assembled through ligation must still be capable of serving as a template for reverse transcription. Although some modified ribonucleotides, such as 2'-OMe, can serve as templates for reverse transcriptase, other useful modified ribonucleotides cannot. This may limit somewhat the identity of the modified ribonucleotides that can be incorporated into the candidate RNA mixture. However, the present invention also contemplates embodiments where reverse transcription is not used to provide the DNA template required for PCR. In these embodiments, a DNA template for PCR is assembled on partitioned RNA candidate mixture molecules (those RNA molecules that interact with the target in the desired manner) in the same way that the RNA candidate mixture molecules themselves were assembled i.e., by contacting the partitioned RNA candidate mixture with libraries comprising randomized and partly randomized DNA fragments, allowing these DNA fragments to anneal to the RNA templates, followed by ligation of the DNA fragments, and PCR amplification of the ligated fragments. As described above, ligation of the DNA fragments can be performed chemically without the use of a DNA ligase. By performing DNA template assembly without reverse transcriptase, it is possible to expand the repertoire of modified bases employed in SELEX even further. Modified bases that are incompatible with RNA polymerase and also with reverse transcriptase can still be incorporated into candidate mixtures using this method. This method will greatly enhance the utility of the SELEX technique by increasing even further the diversity of nucleic acid structure, chemistry and functionality that can comprise a candidate mixture.

The embodiments described above contemplate the use of candidate mixtures of nucleic acid ligands comprising single stranded RNA molecules. However, it will be apparent to those skilled in the art that the methods described herein are readily applicable to candidate mixtures comprising double stranded RNA, single stranded DNA and double stranded DNA.

The Transcription-free SELEX method has a number of additional advantages over the typical SELEX methods. For example, Transcription-free SELEX can produce smaller nucleic acid ligands than typical SELEX methods. This is due to two factors: (1) Increased chemical activity of modified nucleotides, as compared to standard nucleotides; (2) Increased stability of smaller structural motifs, though reduction of backbone charge repulsion. These will be discussed in turn.

The modem, standard set of nucleotides does not provide strong nucleophilic or electrophilic centers, nor does it provide acid-base transitions in neutral pH environments. This lack of reactivity can be compensated somewhat by size: many weak interactions can sum to replace a single strong interaction. This is a disadvantage for nucleic acid ligands, as sequences which specify these many weak interactions will be correspondingly rare and hard to select, and will result in large, hard-to-synthesize sequences if they are selected. Modified fragment libraries which contain highly reactive nucleotides may achieve a smaller nucleic acid ligand size by replacing many weak interactions with one strong one. For instance, a positive charge could be provided by a single modified nucleotide; this could replace the several standard nucleotides in a standard nucleic acid ligand which must fold to form a metal-binding pocket which provides the equivalent charge.

The second path by which Transcription-free SELEX using chemically synthesized fragment libraries can reduce nucleic acid ligand size is by reduction of electrostatic repulsion. Standard phosphodiester nucleic acids contain a single net negative charge per residue. The repulsion between phosphate groups is substantial, even in a standard double helix, and requires many hydrogen-bonding and stacking interactions to compensate, and allow a stable structure to form. Backbone modifications which eliminate this negative charge form much more stable helices. For instance, DNA-PNA (peptide nucleic acid) helices are about 30% more stable than the corresponding DNA-DNA helix. A modified fragment library which incorporates uncharged residues can therefore be expected to have helices and other structural motifs which are more stable than that of a standard nucleic acid library. This increased stability will result in smaller structural motifs, and therefore smaller nucleic acid ligands than the corresponding agents derived from standard SELEX methods.

One of the limiting factors in commercializing nucleic acid ligands, and indeed all oligonucleotide agents, is cost. Considerable effort goes into minimizing the size of candidate oligonucleotide agents in order to minimize this cost. Because the Transcription-free SELEX method can produce smaller nucleic acid ligands than the typical SELEX methods, the method of the instant invention should greatly facilitate the development of more cost-effective nucleic acid ligands.

EXAMPLES

The following examples are described solely for the purpose of illustrating various embodiments of the invention. These examples are not to be construed as limiting the scope of the invention in any sense.

Example 1

Annealing of Random 11-mer RNA to DNA Template

Figure 3:
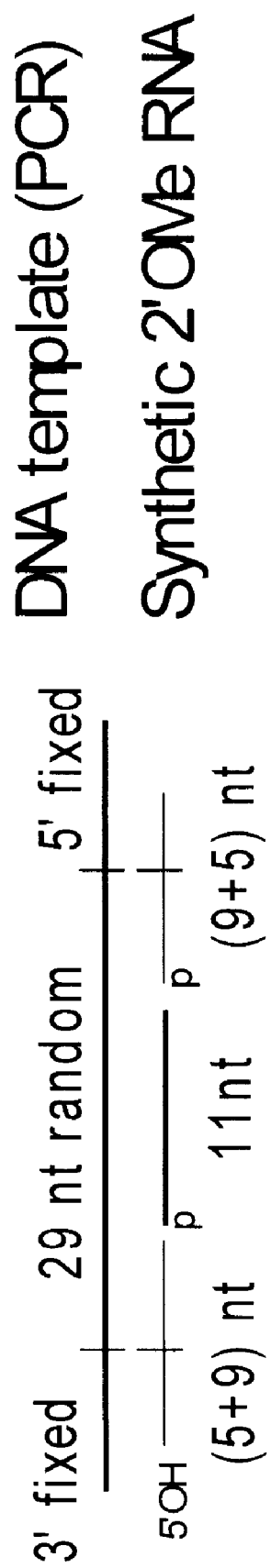
FIG. 3 shows a schematic representation of 3 possible RNA libraries that could be used in a Transcription-free SELEX procedure using a DNA template with a 29 nt randomized region. The individual RNA fragments are shown annealed to the DNA template in the most thermodynamically favorable configuration.

FIG. 3 shows a typical SELEX DNA template library comprising 5' and a 3' fixed sequence regions, and an internal 29 nucleotide random sequence region. Three libraries of RNA are then synthesized:

1. (5+9) nt: each RNA molecule in this library comprises a 5'5 nucleotide fixed sequence complementary to the 3' fixed sequence region of the DNA template; immediately 3' to the 5 nucleotide fixed region, each molecule has a 9 nucleotide random sequence. The 5' end of the individual molecules in the (5+9) nt RNA library bear a hydroxyl (OH) group.

2. (9+5) nt: each RNA molecule in this library comprises a 3'5 nucleotide fixed sequence complementary to the 5' fixed sequence region of the DNA template; immediately 5' to the 5 nucleotide fixed region, each molecule has a 9 nucleotide random sequence. The 5' end of the individual molecules in the (9+5) nt RNA library bear a phosphate (P) group.

3. 11 nt: this comprises a randomized 11 nucleotide RNA sequence; The 5' end of the individual molecules in 11 nt RNA library bear a phosphate (P) group.

Thus, at equilibrium, an 11 nt RNA molecule from the 11 nt library, and 9 nt sequences from the (5+9) and (9+5) nt libraries will completely cover the 29 nt region of each DNA template molecule.

Example 2

Using RNA Libraries to Assemble an RNA Candidate Mixture

The annealing rates for the libraries of Example 1 are calculated as follows:

Number of sequences in a random 11-mer: $4^{11}=4\times10^6$

Annealing rate: $1\times10^7$ $M^{-1}$ $s^{-1}$ (in 0.1 mM CTAB, 65°)

Concentration of DNA template: 1 nmol/50 $\mu l=2\times10^{-5}$ M

Concentration of 11 mer library: 5 nmol/50 $\mu l=1\times10^{-4}$ M

The rate at which a random 11 mer hybridizes is: $1\times10^7$ $M^1$ $s^{-1}\times1\times10^{-4}$ $M/4\times10^6=3\times10^{-4}$ $s^{-1}$.

At this rate, the annealing reaction is over in 1–2 hours.

Because the RNA libraries are in excess, their concentration drives the reaction. The relevant number is the concentration of each sequence, which is the total concentration divided by the complexity. The 9-mers are present at 16-fold higher concentration, and so anneal that much faster. This forces the 11-mer into the proper register. Although misannealing will occur (there are more ways to misanneal than to anneal properly), annealing in the proper register maximizes the number and fraction of bases paired, and so is the most favorable configuration.

What is claimed is:

1. A method for identifying nucleic acid ligands of a target compound, said method comprising:
   a) preparing a candidate mixture of ribonucleic acids;
   b) contacting the candidate mixture of nucleic acids with said target, wherein nucleic acids having an increased affinity to said target relative to the candidate mixture may be partitioned from the remainder of the candidate mixture;
   c) partitioning the increased affinity nucleic acids from the remainder of the candidate mixture;
   d) amplifying the increased affinity nucleic acids to yield a mixture of nucleic acids enriched for nucleic acids with relatively higher affinity and specificity for binding to said target;
wherein said candidate mixture comprises ribonucleic acid molecules, each of said ribonucleic acid molecules being assembled from fragments of RNA comprising randomized sequence.

2. The method of claim 1 wherein said RNA fragments comprise synthetic RNA molecules.

3. The method of claim 2 wherein said synthetic RNA molecules comprise at least one non-naturally occurring ribonucleotide.

4. The method of claim 3 wherein said non-naturally-occurring ribonucleotide is a 2'-OMe ribonucleotide.

5. The method of claim 1 wherein said candidate mixture of nucleic acids is assembled from fragments of RNA by annealing said RNA fragments to a complementary DNA template, and then ligating said annealed RNA fragments.

6. A method for the preparation of nucleic acid ligands to a target, the method comprising:
   (a) providing a DNA template library comprising fixed 3' and 5' sequence regions, and random internal sequences;
   (b) contacting said DNA template library with one or more RNA libraries, each said library comprising synthetic randomized RNA fragments, wherein said RNA fragments anneal to said DNA template, and wherein each said RNA fragment is shorter than said DNA template;
   (c) ligating said RNA fragments together to form a candidate mixture of RNA nucleic acid ligands;
   (d) purifying said candidate mixture of RNA nucleic acid ligands from said DNA template library and contacting said candidate mixture of RNA nucleic acid ligands with a target;
   (e) partitioning RNA nucleic acid ligands in said candidate mixture that interact with the target in a desired manner from those that do not;
   (f) reverse transcribing those RNA nucleic acid ligands that interact with the target in a desired manner to form DNA templates;
   (g) amplifying those DNA templates using the Polymerase Chain Reaction with primers that hybridize to said fixed 5' and 3' sequence regions to form a new DNA template library;
   (h) optionally repeating steps (b)–(g) for a desired number of repetitions.

7. The method of claim 6 wherein a first, second and a third library comprising synthetic randomized RNA fragments are used in step (b), wherein said first library further comprises a fixed RNA sequence complementary to the 5' fixed regions of said DNA template, and wherein said second library further comprises a fixed RNA sequence complementary to the 3' fixed sequence region of said DNA template.

8. The method of claim 7 wherein said first library comprises X ribonucleotides of fixed sequence and Y ribonucleotides of randomized sequence; wherein said second library comprises A ribonucleotides of fixed sequence and B ribonucleotides of randomized sequence; wherein said third library comprises Z ribonucleotides of randomized sequence; and wherein X+Y>Z, A+B>Z, Y>X, B>A, Z>Y, and Z>B.

9. A method for the preparation of RNA nucleic acid ligands to a target, the method comprising:
   (a) providing a DNA template library comprising fixed 3' and 5' sequence regions, and random internal sequences;
   (b) contacting said DNA template library with one or more RNA libraries, each said library comprising synthetic randomized RNA fragments, wherein said RNA fragments anneal to said DNA template, and wherein each said RNA fragment is shorter than said DNA template;
   (c) ligating said RNA fragments together to form a candidate mixture of RNA nucleic acid ligands;
   (d) purifying said candidate mixture of RNA nucleic acid ligands from said DNA template library and contacting said candidate mixture of RNA nucleic acid ligands with a target;

(e) partitioning RNA nucleic acid ligands in said candidate mixture that interact with the target in the desired manner from those that do not;

(f) contacting those RNA nucleic acid ligands that interact with the target in the desired manner with one or more DNA libraries, each said library comprising synthetic randomized DNA fragments, wherein said DNA fragments anneal to said RNA nucleic acid ligands, and wherein each said DNA fragment is shorter than said RNA nucleic acid ligands;

(g) ligating said DNA fragments together to form new DNA templates;

(h) amplifying those new DNA templates using the Polymerase Chain Reaction with primers that hybridize to said fixed 5' and 3' sequence regions to form a new DNA template library;

(i) optionally repeating steps (b)–(h) for the desired number of repetitions.

* * * * *